United States Patent
Krauβ et al.

(10) Patent No.: US 9,211,104 B2
(45) Date of Patent: Dec. 15, 2015

(54) SELECTION METHOD FOR TWO CONTRAST MEDIA FOR USE IN A DUAL-ENERGY CT EXAMINATION, CONTRAST MEDIA COMBINATION AND GENERATION OF CT IMAGES USING A CONTRAST MEDIA COMBINATION AND DIFFERENT ENERGY SPECTRA

(75) Inventors: Bernhard Krauβ, Burgthann (DE); Hubertus Pietsch, Kleinmachnow (DE)

(73) Assignee: BAYER INTELLECTUAL PROPERTY GMBH, Monheim (DE)

( * ) Notice: Subject to any disclaimer, the term of this patent is extended or adjusted under 35 U.S.C. 154(b) by 1648 days.

(21) Appl. No.: 12/451,648

(22) PCT Filed: May 19, 2008

(86) PCT No.: PCT/EP2008/056115
§ 371 (c)(1), (2), (4) Date: Nov. 23, 2009

(87) PCT Pub. No.: WO2008/142048
PCT Pub. Date: Nov. 27, 2008

(65) Prior Publication Data
US 2010/0135557 A1 Jun. 3, 2010

(30) Foreign Application Priority Data
May 24, 2007 (DE) .......... 10 2007 024 158

(51) Int. Cl.
*A61B 8/08* (2006.01)
*A61B 6/00* (2006.01)
*A61B 6/03* (2006.01)

(52) U.S. Cl.
CPC ............. *A61B 6/482* (2013.01); *A61B 6/032* (2013.01)

(58) Field of Classification Search
None
See application file for complete search history.

(56) References Cited

U.S. PATENT DOCUMENTS

2004/0101088 A1* 5/2004 Sabol et al. .......... 378/4
2004/0101089 A1 5/2004 Karau et al.
(Continued)

FOREIGN PATENT DOCUMENTS

DE 10355094 A1 6/2004
DE 102005026940 A1 12/2006
(Continued)

OTHER PUBLICATIONS

Min Qu et al., Combined photoacoustic and magneto-motive ultrasound imaging, Department of Biomedical Engineering University of Texas at Austin, Austin, TX 78712, Proc. of SPIE, vol. 7564 756433-1-756433-7.
(Continued)

*Primary Examiner* — Unsu Jung
*Assistant Examiner* — Joseph M Santos Rodriguez
(74) *Attorney, Agent, or Firm* — Harness, Dickey & Pierce, P.L.C.

(57) ABSTRACT

A method is disclosed for selecting two contrast agents to be used in a dual energy CT examination of a patient. In at least one embodiment, the method includes determining the gradient of a connecting line between a first material or a first tissue type and a second material or second tissue type in an HU value diagram of the energy-specific HU values, selecting a first contrast agent with an enhancement gradient which is significantly greater than the determined base gradient, and selecting a second contrast agent, the enhancement of which lies in the significance region of the determined base gradient. A contrast agent combination selected in the fashion is also disclosed in at least one embodiment, as well as the generation of CT images using a contrast agent combination selected in the fashion and using different energy spectra.

27 Claims, 4 Drawing Sheets

(56) References Cited

U.S. PATENT DOCUMENTS

| | | |
|---|---|---|
| 2005/0084069 A1 | 4/2005 | Du |
| 2007/0025514 A1 | 2/2007 | Lawaczeck et al. |
| 2007/0217570 A1 | 9/2007 | Grasruck et al. |
| 2008/0253508 A1* | 10/2008 | Krauss .................. 378/19 |
| 2008/0310582 A1 | 12/2008 | Flohr et al. |
| 2010/0135557 A1 | 6/2010 | Krauss et al. |

FOREIGN PATENT DOCUMENTS

| | | |
|---|---|---|
| DE | 102005052368 A1 | 5/2007 |
| DE | 102006009222 B | 9/2007 |
| EP | 2150179 B1 | 4/2013 |

OTHER PUBLICATIONS

Johnson, Thorsten R.C. et al., "Material differentiation by dual energy CT: initial experience", European Radiology Online, Bd. 17, Nr. 6, Dec. 2006, pp. 1510-1517, XP002497949; Others.

Canadian Office Action for Canadian Application No. 2,706,188 dated Dec. 17, 2014.

\* cited by examiner

SELECTION METHOD FOR TWO CONTRAST MEDIA FOR USE IN A DUAL-ENERGY CT EXAMINATION, CONTRAST MEDIA COMBINATION AND GENERATION OF CT IMAGES USING A CONTRAST MEDIA COMBINATION AND DIFFERENT ENERGY SPECTRA

PRIORITY STATEMENT

This application is the national phase under 35 U.S.C. §371 of PCT International Application No. PCT/EP2008/056115 which has an International filing date of May 19, 2008, which designates the United States of America, and which claims priority on German patent application number DE 10 2007 024 158.7 filed May 24, 2007, the entire contents of each of which are hereby incorporated herein by reference.

FIELD

At least one embodiment of the invention generally relates to a method for selecting two contrast agents to be used in a dual energy CT examination of a patient, a method for generating CT images of a patient and/or a combination of two contrast agents, provided for application in a CT examination with at least two different X-ray energy spectra for assessing the proportion of a first and a second tissue type, with a connecting line with a base gradient being formed between the first and second tissue type in an HU value diagram. At least one embodiment of the invention furthermore also generally relates to a contrast agent combination and/or to the generation of CT images using this contrast agent combination, taking into account two different energy spectra.

BACKGROUND

Methods for determining a contrast agent concentration in the body material of a human or animal patient and for simultaneously differentiating between two different tissue types are widely known. In particular, the following method variants are used in this process:

Previously, two different techniques were known for determining a contrast agent concentration using computed tomography (CT). In the first technique, a computed tomography image of the body region in which the contrast agent concentration is intended to be measured can in each case be recorded before and after contrast agent is administered. After registering the two CT images obtained in the process, they are subtracted from one another in order to obtain the increased X-ray attenuation values caused by the contrast agent for every pixel or voxel. This increase in the X-ray attenuation values is pro-portional to the concentration of the contrast agent. However, as a result of this requiring the computed tomography images at different times, registration and/or movement artifacts can occur and can lead to an erroneous determination. Furthermore, if a contrast agent is used which only accumulates slowly in the body material, an undesirably long waiting period has to be observed between the two computed tomography images.

The second known technique utilizes the use of a multi-energy computed tomography scanner in order to record, simultaneously, two computed tomography images with different spectral distribution of the X-ray radiation, i.e. with different X-ray energy. In a variant of this technique, the image data records for both X-ray energies are first of all reconstructed separately from each other. Subsequently, the measured X-ray attenuation values for each voxel are decomposed into the molecular density of two base materials (2 material decomposition), the contrast agent constituting one base material. The two equations resulting from the decomposition can be used to determine the two unknowns for each voxel: the concentrations of the two base materials. However, this technique does not supply satisfactory results for a number of body materials because the decomposition for all material components comprised in the body material is not readily foreseeable. Thus, the application of this technique for determining the contrast agent concentration in the liver (which generally also contains a relatively large proportion of fat) results in a mixture of the two base materials which is difficult to interpret.

Furthermore, reference is made to the applicant's patent application with the file reference DE102006009222.8, which is not a prior publication and makes possible a 3 material decomposition of an examined region using a dual energy CT examination. Herein, the region under examination, preferably a human or animal patient, is subdivided into two different tissue types and the quantitative occurrence of a contrast agent is determined at the same time.

In this last-mentioned method, two computed tomography images of the body material are recorded using a multi-energy computed tomography scanner, in particular a so-called dual energy computed tomography scanner, at two different spectral distributions of the X-ray radiation. Recording using the two different X-ray energies is preferably performed simultaneously in this case. Two image data records which contain X-ray attenuation values x are reconstructed in a known fashion from the measurement data of the computed tomography images. Here, X-ray attenuation values can be understood to be both the attenuation coefficients $\mu$ and values, such as the CT value, derived therefrom.

In the present method, the X-ray attenuation values x for each voxel of interest in the two image data records are decomposed into X-ray attenuation values of three material components. These three material components are the two different material components of the body material and the substance whose concentration is intended to be determined. It goes without saying that the two different material components of the body material do not have to be chemically pure materials, but they can also constitute material mixtures. In the present method, the X-ray attenuation values are decomposed under the assumption that the X-ray attenuation value $x_M$ of the body material M without the substance is made up of the X-ray attenuation values $x_{M1}$, $x_{M2}$ of the first and second material component according to the following equation:

$$x_M = f \cdot x_{M1} + (1-f) \cdot x_{M2},$$

where f corresponds to a volume proportion of the first material component in the body material. The concentration of the substance in each voxel of interest is then determined on the basis of this decomposition. This is possible because for each voxel there are respectively two equations corresponding to the two image data records with a total of two unknowns: the volume proportion f of the first material component and the concentration c of the substance accumulated in the body material.

According to one refinement of this method, the concentration of the substance is therefore also determined by the solution of this system of equations comprising the following two equations:

$$x_{E1} = c \cdot x_{KM,E1} + f \cdot x_{M1,E1} + (1-f) \cdot x_{M2,E1}$$

$$x_{E2} = c \cdot x_{KM,E2} + f \cdot x_{M1,E2} + (1-f) \cdot x_{M2,E2}$$

where $x_{E1/E2}$ corresponds to the X-ray attenuation values in the two image data records at the different spectral energy distributions or energies E1 and E2 of the X-ray radiation and c corresponds to the concentration of the substance in the body material. The X-ray attenuation values $x_{M1}$ and $x_{M2}$ at the different X-ray energies E1, E2 are known and can, for example, be gathered from a table. The same holds true for the X-ray attenuation value $x_{KM}$ of the substance to be determined. Said attenuation value can, if need be, also be determined in advance by a separate calibration measurement, for example by using a water phantom.

The present method and the associated device utilize the recognition that in reality many materials only occur in the human and animal body with an approximately constant density. Using this property as a starting point, this means that, in a CT image, even mixtures of two materials do not have arbitrary X-ray attenuation values. This was able to be verified experimentally for liver tissue. The CT value of liver tissue decreases linearly with an increasing proportion of stored fat. It is also known that the difference between the X-ray attenuation values at different tube voltages of the computed tomography scanner, i.e. at different X-ray energies, is a linear function of the fat content. This relationship can also be extended to other body materials and is utilized in the present method and the associated device.

Although all of the abovementioned methods allow examinations to be performed at different times with a number of contrast agents, the amount of radiation dose used increases proportionally with the number of examinations and the expenditure of time increases correspondingly.

SUMMARY

At least one embodiment of the invention is directed to an improved method for the examination with, and display of, two different contrast agents present in a patient, wherein a dose reduction is desirable and, for this purpose, the correct selection of the two contrast agents is intended to be made and an optimized contrast agent combination is intended to be determined.

The inventors have recognized, in at least one embodiment, that it is possible to perform a CT examination using a 3 material decomposition method whilst simultaneously applying two contrast agents, with the correctly selected combination of the two contrast agents affording the possibility of firstly obtaining a pure contrast agent image of the first contrast agent and obtaining a second image representation which corresponds to a single energy image with only a single contrast agent. To this end, it is first of all necessary to select a combination of two contrast agents having a first contrast agent with an enhancement gradient which is as large as possible. The enhancement gradient is considered to be the ratio of the HU (Hounsfield Unit) value increases when adding a contrast agent, i.e. the direction or gradient of a connecting line between different contrast agent concentrations in the HU value diagram, to different energy spectra. Under "enhancement", this connecting line is considered to be a vector.

Figure 6:
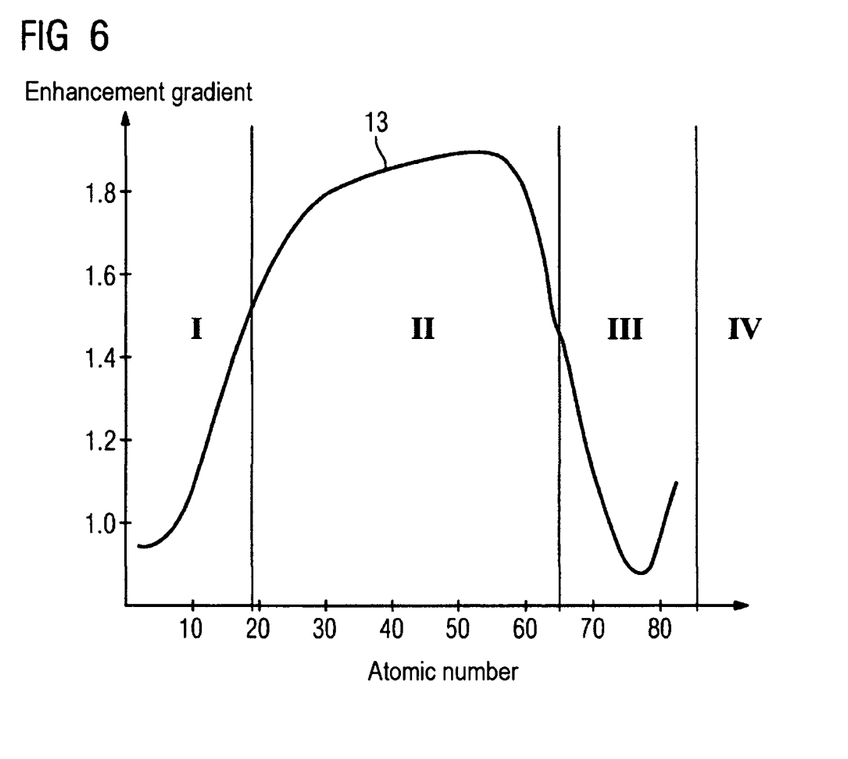
FIG. 6 shows a schematic illustration of the enhancement gradient plotted against atomic number.

This enhancement gradient now needs to be that large that an accumulation of a tissue type leads to a contrast increase plotted in an HU value diagram, which increase lies in a significantly distinguishable fashion above the connecting line between two examined tissue types plotted in the HU value diagram. Since body materials such as fat or muscle tissue are substantially composed of light atoms up to an atomic number of 8 (oxygen), the base gradient generally lies in the region of 1. As illustrated in FIG. 6, it is therefore easy to use a contrast agent which comprises an element with an atomic number greater than 19. Furthermore, a second contrast agent should be selected which has an enhancement gradient which corresponds to the base gradient between the two examined tissue types or which at least does not deviate in a significant and distinguishable fashion from this base gradient. Thus, a first or second tissue type in which the second contrast agent accumulates can at first not be distinguished mathematically from a combination of the first and second tissue type when applying the 3 material decomposition method. If, additionally, a second contrast agent which preferably accumulates in the tissue type lying in the direction of higher HU values in the HU value diagram is also selected, a larger distance between the measured HU values, that is to say a contrast increase between the first and the second tissue, is additionally ensured. Moreover, it is also possible to differentiate between regions which contain the second tissue and take in contrast agent and regions which do not.

Reference is made to the fact that within the scope of the embodiments of invention, the term tissue type should not constitute a restriction in respect of the considered materials; for example, air can also be used as a tissue type.

At least one embodiment of the selection method for the contrast agents can also be extended to the known 2 material decomposition because this is identical to a 3 material decomposition in which air is selected as first material and e.g. muscular tissue as second body material.

In at least one embodiment, if a pure contrast agent image and a virtual native image are generated using the method described in the patent application with the file reference DE 10 2006 009 222.8—the contents thereof should be completely incorporated herein into this application by reference—the contrast agent image only includes information in respect of the first contrast agent while the virtual native image presents information in respect of the two tissue types and the second contrast agent. By way of example, this firstly affords the possibility of imaging a representation of the blood vessels in a liver and, simultaneously, showing an illustration of the liver with an improved resolution in respect of the contrast between normal liver tissue and fatty liver tissue, or between healthy liver tissue and a tumor which does not accumulate a contrast agent.

An important point of the realization described above lies in the fact that it is possible to generate a desired enhancement in an HU value diagram which lies on the connecting line between two materials in the HU value diagram; this being made possible by a defined and, in terms of its proportions, predetermined combination of different contrast agent elements or contrast agent components of a contrast agent. By way of example, this can be effected by selecting a contrast agent element, e.g. from the group of the lanthanides, for the contrast agent, which contrast agent element generates a corresponding enhancement or a corresponding enhancement gradient. It is also possible for a number of contrast agent elements, preferably at least in part from the group of the lanthanides, to be attached to the molecular configuration of the contrast agent, which elements, in total, lead to the desired enhancement. Finally, it is also possible for a mixture of different contrast agent components to be used at a predetermined ratio with respect to one another, which, in total, generate the desired enhancement, as a contrast agent, with care being taken to ensure that these individual contrast agent components have the same pharmacokinetic properties, that is to say their behavior in the body is identical and hence no separation effects occur, for example by different adsorption on tissue structures or the like.

In accordance with these realizations, in at least one embodiment the inventors propose a method for selecting two contrast agents to be used in a dual energy CT examination of a patient, comprising the following method steps:

scanning the patient taking into account at least two different radiation spectra and reconstructing a first image data record on the basis of the first radiation spectrum and a second image data record on the basis of the second radiation spectrum, determining an HU value diagram from the two image data records, calculating the gradient (=base gradient) of a connecting line between a first material or a first tissue type and a second material or second tissue type in the HU value diagram of the energy-specific HU values, selecting a first contrast agent from a number of contrast agents, each with a known enhancement gradient, with an enhancement gradient which is significantly greater than the determined base gradient, selecting a second contrast agent, the enhancement gradient of which lies in the significance region of the determined base gradient.

To this end, reference is made to the fact that the significance region of the determined base gradient is in each case specific for the utilized CT system and is intended to represent that region in which a deviation of the enhancement gradient from the base gradient can be detected unambiguously.

According to at least one embodiment of the invention, a tissue type can replace both materials or one of the materials. In the following text, the term tissue type represents both material and tissue type.

It is advantageous if the significance is determined at least in respect of a subsequently performed component decomposition method, the utilized examination dose, the observed energy spectra and the system properties of the CT system.

The first tissue type can for example be considered to be a glandular tissue, preferably a liver tissue. The second tissue type can preferably be considered to be fatty tissue. Furthermore, the base gradient can be determined from a multiplicity of CT liver examinations with different degrees of pathological fatty metamorphosis of liver.

Furthermore, in a particular variation of at least one embodiment of the invention, an iodine-containing contrast agent can be used as first contrast agent, while a contrast agent with components from the group of the lanthanides is used as second contrast agent. For this purpose, it is furthermore possible for a combination of at least two lanthanides to be used in the second contrast agent.

It is preferable for a contrast agent which preferably accumulates in the cardiovascular system to be selected as first contrast agent and a contrast agent which preferably accumulates in cells of the first tissue type to be selected as second contrast agent.

Furthermore, a method for generating CT images of a patient having two different contrast agents, wherein the second contrast agent has an enhancement whose gradient in an HU value diagram corresponds to the radiation spectra of the gradient between two different materials or tissue types (=base gradient) used in this HU value diagram, comprising the following method steps, is proposed:

scanning the patient using a CT system, taking into account at least two different radiation spectra and reconstructing a first image data record on the basis of the first radiation spectrum and a second image data record on the basis of the second radiation spectrum, generating a third image data record solely comprising the local concentration of the first contrast agent and generating a fourth image data record comprising the tissue types, including the local concentration of the second contrast agent, by solving linear systems of equations for each pixel/voxel of the first and second image data record, which describe the relationship between absorption and components concentration of the two tissue types and the first contrast agent, output of at least the third and/or fourth image data record.

In the process, the contrast agents can be selected in accordance with the previously described method for selecting two contrast agents.

In particular, the following linear system of equations can be solved for each pixel/voxel:

$$x_{E1} = c_{K1} * x_{K1,E1} + f * x_{G1,E1} + (1-f) * x_{G2,E1}$$

$$x_{E2} = c_{K1} * x_{K1,E2} + f * x_{G1,E2} + (1-f) * x_{G2,E2}$$

with the following variables being used:
f=proportion of the first tissue type G1,
(1−f)=proportion of the second tissue type G2,
$c_{K1}$=concentration of the first contrast agent K1,
$x_{K1,E1}$=known X-ray attenuation value of the first contrast agent K1 in respect of the first energy spectrum E1,
$x_{K1,E2}$=known X-ray attenuation value of the first contrast agent K1 in respect of the second energy spectrum E2,
$x_{G1,E1}$=known X-ray attenuation value of the first tissue type G1 in respect of the first energy spectrum E1,
$x_{G1,E2}$=known X-ray attenuation value of the first tissue type G1 in respect of the second energy spectrum E2,
$x_{G2,E1}$=known X-ray attenuation value of the second tissue type G2 in respect of the first energy spectrum E1,
$x_{G2,E2}$=known X-ray attenuation value of the second tissue type G2 in respect of the second energy spectrum E2.

It is furthermore proposed that measurements are performed with two different energy spectra of the utilized radiation with at least one detector integrating over at least the used energy ranges in order to differentiate the absorption property of the utilized contrast agents with respect to different energy spectra.

Measurements can also be performed with one energy spectrum of the utilized radiation and with at least one detector selective at at least two different energy ranges in order to differentiate the absorption property of the utilized contrast agents with respect to different energy spectra.

Furthermore, within the scope of at least one embodiment of the invention, a combination of two contrast agents is proposed, provided for application in a CT examination with at least two different discretely examined X-ray energy spectra for assessing the proportion of a first and a second tissue type, with a connecting line with a base gradient being formed between the first and second tissue type in an HU value diagram, the combination comprising:

a first contrast agent having a gradient in respect of the at least two utilized energy spectra in an HU value diagram, the gradient being significantly greater than the base gradient, a second contrast agent having a gradient in respect of the at least two utilized energy spectra in the HU value diagram, the gradient lying in the significance region of the base gradient.

For this purpose, the first tissue type can preferably be a glandular tissue, preferably a liver tissue, and the second tissue type can preferably be a pathological glandular tissue, preferably a pathological liver tissue corresponding to the tissue of a fatty liver.

It is furthermore advantageous for the first contrast agent to preferably accumulate in the cardiovascular system and for the second contrast agent to preferably accumulate in cells of the first tissue type or to adsorb on the tissue cells contained therein.

According to at least one embodiment of the invention, at least one contrast agent can comprise a single lanthanide, as a result of which the desired enhancement is generated, or at least one contrast agent can consist of a mixture of a plurality of contrast agent components with at least differing lanthanides, wherein the individual contrast agent components should have the same pharmacokinetic properties and, in total, the desired enhancement.

On the other hand, at least one contrast agent can also comprise a molecular complex which is occupied by different contrast-providing elements with a predetermined stoichiometric ratio such that the desired enhancement is attained.

Finally, the inventors also propose, in at least one embodiment, the use of the inventive combination of two contrast agents in the method described initially.

BRIEF DESCRIPTION OF THE DRAWINGS

In the following text, at least one embodiment of the invention will be described in more detail on the basis of an example embodiment and with aid of the figures, with only the features required for understanding the invention being illustrated. In the process, the following reference signs are used: 1: CT system; 2: first X-ray tube; 3: first detector; 4: second X-ray tube; 5: second detector; 6: gantry housing; 7: patient; 8: patient couch; 9: system axis, z-axis; 10: control and computational unit; 11: contrast agent applicator; 12: 3 component decomposition; m: base gradient between tissue G1 and tissue G2; $m_1$: enhancement gradient of the first contrast agent K1; $m_2$: enhancement gradient of the second contrast agent K2; A1: performing a CT scan with a first energy spectrum; A2: performing a CT scan with a second energy spectrum; B1: CT image data record of the CT scan using the first energy spectrum; B2: CT image data record of the CT scan using the second energy spectrum; $B_{K1}$: calculated image data record illustrating the distribution of the first contrast agent K1; $B_{G1+G2+K2}$: calculated image data record illustrating the distribution of the second contrast agent K2 and the first and second tissue type G1 and G2; G1: first tissue type; G2: second tissue type; μ: X-ray absorption coefficient; μ(80 kVp): measured absorption coefficients at 80 kVp X-ray radiation; μ(140 kVp): measured absorption coefficients at 140 kVp X-ray radiation; I-IV: Atomic number ranges.

In detail.

DETAILED DESCRIPTION OF THE EXAMPLE EMBODIMENTS

In accordance with an embodiment of the invention, the concentration of a contrast agent in body materials, in particular liver tissue, is intended to be measured using computed tomography, with another contrast agent being applied at the same time in which only the CT value increase relative to the surroundings but not the precise concentration is of interest.

Achieving the object requires two particular components: the X-ray absorption must firstly be measured at least in respect of two different energy spectra; this can preferably be effected using a dual energy CT scanner which affords reconstruction of two independent images for at least one axial slice through the patient, which images were generated with different effective X-ray spectra. This can be implemented, for example, by simultaneously scanning at two different tube voltages in a CT scanner with two X-ray tubes (=dual source CT). Alternatively, it is possible, for example, to use a simple CT scanner with an energy selective detector. All that is important is that the different absorption effects can be observed in two different energy ranges. In the following text, the term dual energy CT should represent an energy-specific CT in a generally applicable fashion.

Figure 1:
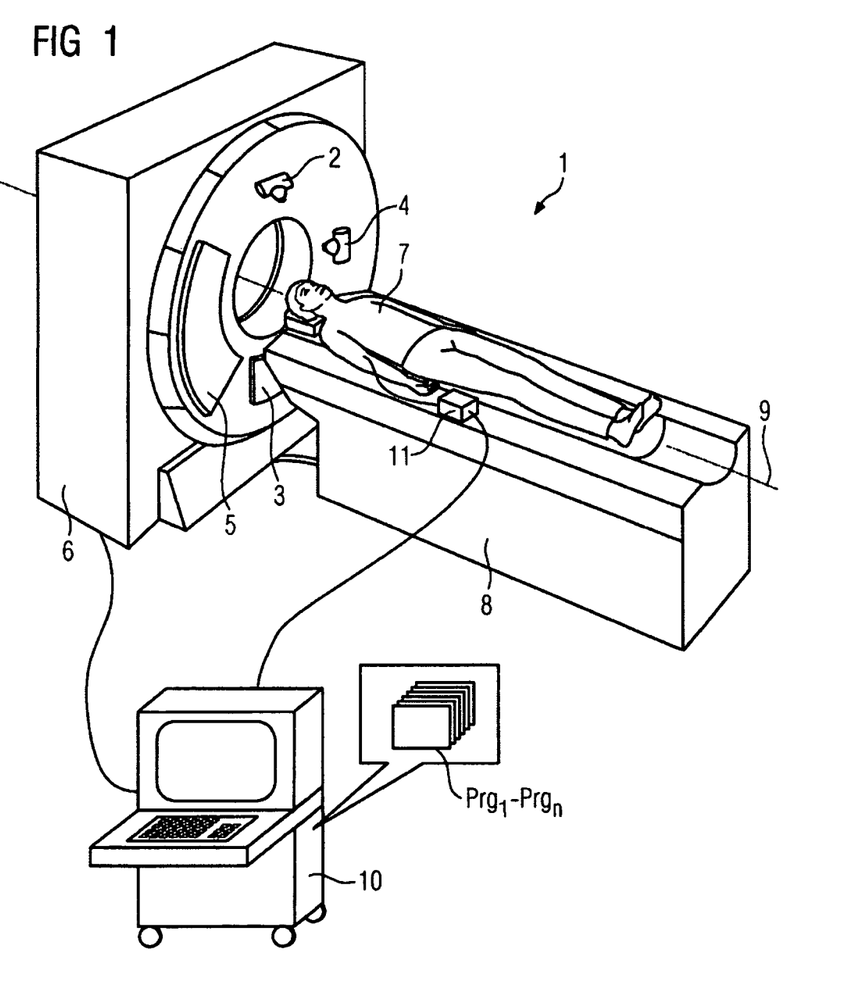
FIG. 1 shows a schematic illustration of a computed tomography scanner.

An example of such a CT system 1 is illustrated in FIG. 1. This CT system 1 has a gantry housing 6 in which two X-ray tubes 2 and 4 with opposing detector systems 3 and 5 are arranged in an angularly offset fashion and rotate about a system axis 9 in order to scan the patient 7 while the patient 7 is displaced through the measurement region of the CT system, along the system axis 9 by way of the controllable patient couch. In the example illustrated in this case, the two X-ray tubes 2 and 4 are operated at different acceleration voltages and so the two utilized X-ray spectra substantially differ from one another and also supply different absorption values in the associated detectors when the patient is irradiated.

A control and computational unit 10 is used for controlling, reconstructing and executing the method according to the invention; said unit comprises in its storage computer programs $Prg_1$-$Prg_n$ which execute the control and reconstruction during operation. At least one program $Prg_x$ is also part of these programs and it executes a method according to the invention. The control and computational unit also controls a contrast agent applicator 11, with the aid of which the contrast agents, selected according to an embodiment of the invention, can be applied.

Specifically selected contrast agents are used to carry out the method according to an embodiment of the invention, which contrast agents can be distinguished using dual energy CT. A further requirement is that at least the second contrast agent, in terms of its absorption properties, has to be designed or selected specifically for the utilized effective X-ray spectra and the observed tissue surroundings.

A precondition for the algorithmic achievement of the object is a known three material decomposition, as is described in the patent application with the file reference DE 10 2006 009 222.8. It can also be applied analogously for a conventional 2 material decomposition.

In the following text, the method of an embodiment will be described specifically for a liver examination, without this intending to restrict the general applicability. Once a person skilled in the art knows this specific solution, he or she is readily able to extend the specific solution to different other tissue combinations.

If the liver tissue in a patient is examined, it is ideally composed of only glandular tissue, referred to as tissue in the following text, and fat with in each case a constant density. As a result of this assumption, the following linear dependence of the HU value x as a function of the fat content f then holds:

$$x = f \times x_{fat} + (1-f) \times x_{tissue}.$$

Figure 2:
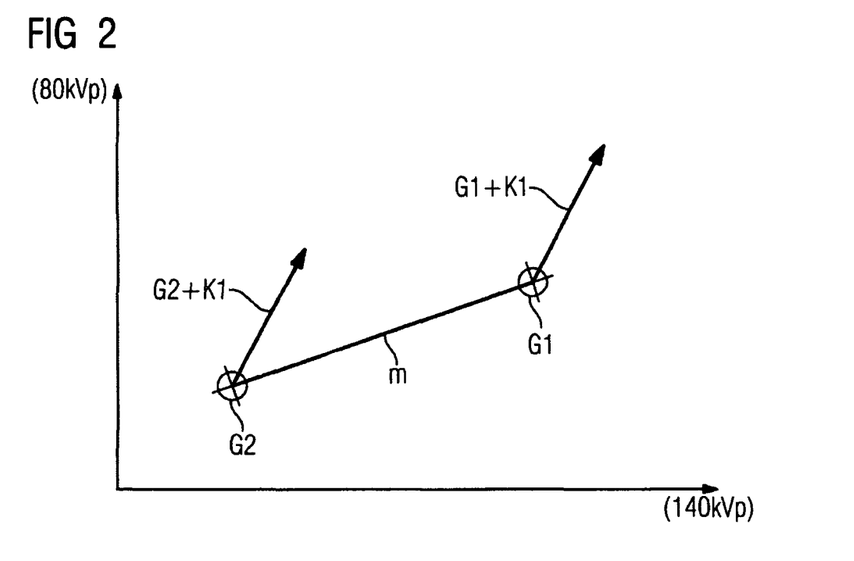
FIG. 2 shows an HU value diagram with plotted HU values for a first and a second tissue.

Here, $x_{fat}$ and $x_{tissue}$ refer to the HU values depending on the tube voltage of the pure materials mentioned in the indices. If, as illustrated in FIG. 2, the determined HU value at 80 kVp acceleration voltage is plotted against the HU value at 140 kVp acceleration voltage in an HU value diagram, the HU value pairs of HU values for all possible mixtures of fat and tissue lie on a straight line with a gradient m which corresponds to the base gradient within the scope of the invention. In FIG. 2, the HU value diagram is illustrated for the two radiation spectra with 80 kVp on the ordinate and 140 kVp on the abscissa, with the points G1 and G2 representing the HU value pairs of tissue and fat.

If a first contrast agent K1, e.g. iodine, is now added, the HU values in both spectra increase substantially. This is illustrated in FIG. 2 by the arrows G1+K1 and G2+K1. The gradients of these illustrated arrows correspond to the enhancement of the contrast agent K1 in respect of the two utilized energy spectra or the examined energy ranges. Since the contrast agent cause significant absorption even in low concentrations, it approximately holds true that the HU value increases linearly with the concentration c of the admixed contrast agent K1, with the absorption per molar concentration of the contrast agent not depending on the organic material, here the specific fat/tissue mixture. The resultant HU value in respect of the 80 kVp or 140 kVp spectrum then results from:

$$x_{80/140} = f \times x_{fat80/140} + (1-f) \times x_{tissue80/140} + cx_{contrast\ agent80/140}.$$

Using the three component decomposition mentioned initially, it is thus possible to calculate the fat content f and the contrast agent concentration c of the one contrast agent K1 by measuring the energy-specific HU values for every point in the HU value diagram.

It is obvious that this method only works if the direction of the vectors plotted in FIG. 1, which illustrates the increase in the CT value by the contrast agent, i.e. the enhancement of the contrast agent, spans a sufficiently large angle with respect to the fat/tissue connecting straight line because otherwise the linear system of equations used to calculate the component decomposition reacts very sensitively to noise. In the extreme case in which the enhancement or the contrast agent vector is parallel to the connecting straight line, the system of equations cannot be solved at all.

In the case of existing contrast agents, which typically comprise heavy atoms up to iodine, this is generally not a problem. Iodine-containing contrast agents in particular are even optimally suited to the method because they have a large enhancement gradient.

Figure 3:
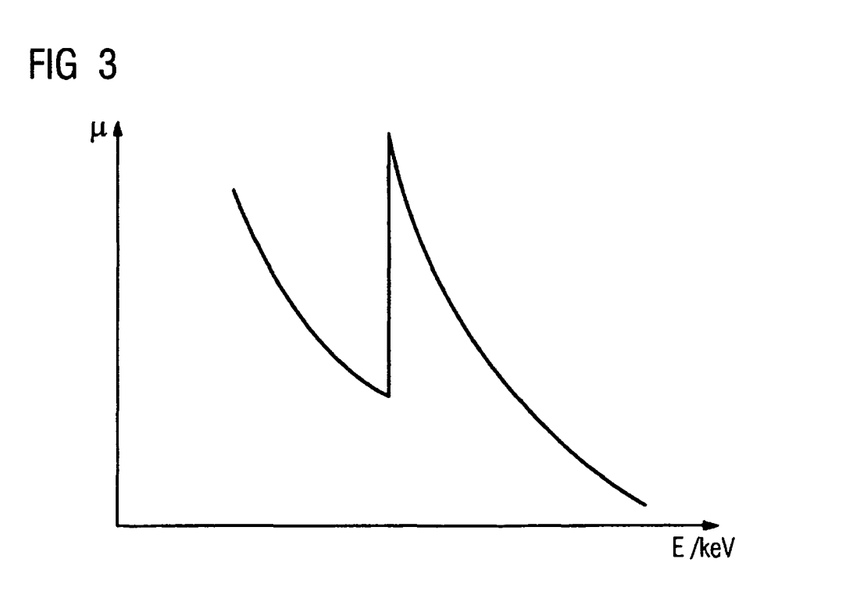
FIG. 3 shows a schematic profile of the absorption coefficients with a K-edge over the photon energy.

In order to devise a suitable contrast agent K2 for the method according to an embodiment of the invention, the following physical background knowledge is required: The absorption spectrum of iodine is dominated by the photoelectric effect with release of an electron from the K shell of iodine. This absorption drops sharply for photons which do not have sufficient energy for this process (<33 keV) because then only L shell electrons contribute to the absorption. For typical CT scanners, this "K edge" lies below the utilized photon energy. A schematic profile of the absorption is illustrated in FIG. 3.

The K edge of elements with a higher atomic number moves into the energy range used by the dual energy CT scanner from below. As a result, the ratio of the absorption at the lower tube voltage relative to the absorption at the higher tube voltage decreases at a constant concentration. For suitably high atomic numbers, the reconstructed HU value at the lower tube voltage can even become smaller than the HU value at the higher tube voltage. For example, in the case of currently available scanners from the applicants, this transition lies in the region of the lanthanides.

Thus, in particular, it is possible to devise a contrast agent K2 which, in the 80 kVp/140 kVp HU value diagram illustrated in FIG. 2, has an increase vector which lies parallel to the connecting line between fat and tissue. In particular, it is possible to find a combination of two contrast agents K1 and K2, wherein the first contrast agent K1 has an enhancement with a gradient which unambiguously and significantly lies above the base gradient between two tissue types G1 and G2, and wherein the second contrast agent has an enhancement which corresponds to the aforementioned base gradient, at least within the error tolerance range of the CT system.

Figure 4:
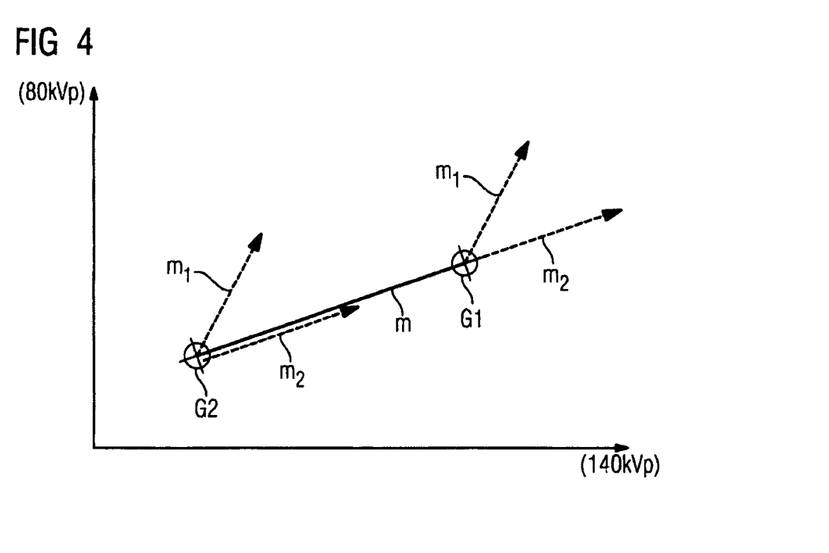
FIG. 4 shows an HU value diagram for two tissue types, including the enhancement from an inventive combination of two contrast agents.

Such a combination is illustrated schematically in FIG. 4. Here, the points G1 and G2 of the HU value pairs are plotted for the two tissue types: liver tissue and fat tissue. The connecting straight line G1-G2 between these points has the gradient m, with vectors with the gradients $m_1$ and $m_2$ originating from each point G1 and G2, which vectors correspond to the enhancement of the contrast agents K1 and K2. The vector with the gradient $m_2$ at G2 is arranged slightly offset in respect of the connecting line G1-G2 for improved clarity. In this case, the contrast agent K2 was selected or "designed" such that its enhancement gradient $m_2$ corresponds to the base gradient m.

If the described three material decomposition is now performed in these conditions, the concentration of the contrast agent K1 (e.g. with iodine as a main component) is determined correctly, while the contrast agent K2 (e.g. with erbium as a main component) is interpreted as a mixture of fat and tissue, with the factor f in the result also being able to be less than zero.

The diagnostic use of the method is developed in particular if a virtual native image is calculated. In this image, the contrast agent K2 leads to a corresponding increase in HU value. Thus what is obtained is, on the one hand, a pure contrast agent image for the contrast agent K1 and a "virtual native image" which looks like a traditional single energy CT image using the contrast agent K2.

This method is advantageous in particular if the contrast agents illustrate different functional aspects of the body tissue, e.g. vascularization and cell activity. To this end, as a carrier substance/carrier molecule of the two contrast agents, a component mainly accumulating in the cardiovascular system can be selected on the one hand for the first contrast agent K1 with the higher enhancement gradient and a different component mainly accumulating in pathological tissue cells, in particular liver cells, can be selected as carrier substance/ carrier molecule for the second contrast agent. Compared to the method of registration/subtraction, this has the advantage that there are no registration artifacts. Moreover, only a single CT scan is required and not two scans as is the case in the described alternative method and so time and dose are saved.

Figure 5:
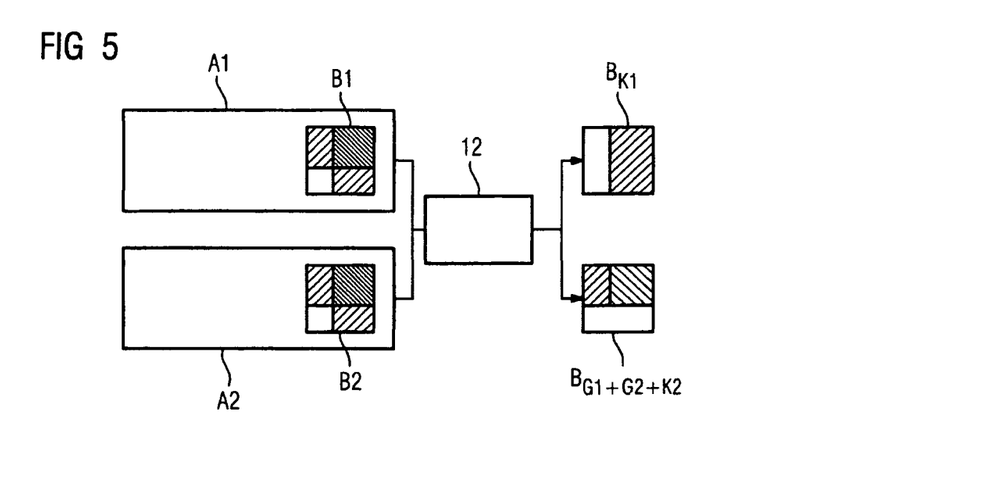
FIG. 5 shows a schematic illustration of the 3 material decomposition.

The method according to an embodiment of the invention can be illustrated in an abbreviated fashion in accordance with FIG. 5. Here, on the left-hand side, the two image data records B1 and B2 are recorded A1 and A2, taking into account different energy ranges, for example 50-80 keV and 70-140 keV. The contrast agents selected according to an embodiment of the invention are used for this purpose. Subsequently, a 3 component decomposition is performed in method step 12, for example a 3 component decomposition in accordance with the method described in the patent application with the file reference DE 10 2006 009 222.8. This then results in, on the one hand, an illustration $B_{K1}$ of only the first contrast agent K1 and, on the other hand, an illustration $B_{G1+G2+K2}$ of the two tissue components G1 and G2 with the contrast agent K2. Thus, the first image or the first image data record corresponds to a segmentation of the first contrast agent K1, while the second image or the second image data record corresponds to a single image of a CT with an energy range, using the second contrast agent K2.

Finally, FIG. 6 shows the profile 13 of the enhancement gradient, that is to say the ratio of the HU value increases at two X-ray spectra of 80 kVp X-ray radiation and 140 kVp X-ray radiation used in an exemplary fashion for a CT system, likewise used in an exemplary fashion, over the atomic number of the contrast-generating element. The contrast-generating element is, in an exemplary fashion, assumed to be dissolved in water. The diagram shows four regions I to IV, with the region I comprising the elements which are unsuitable as a contrast agent due to a lack of absorption and a low enhancement gradient. The region II contains the elements which are suitable for the first contrast agent (up to iodine/early lanthanides). The region III contains the elements which are suitable for a second contrast agent, in particular the lanthanides. At the same time, the elements located in region IV are unsuitable for contrast agents since they are predominately radioactive.

It is understood that the abovementioned features of the invention can be used not only in the respectively specified combination, but also in other combinations or on their own, without departing from the scope of the invention.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

The invention claimed is:

1. A method for selecting two contrast agents to be used in a dual energy CT (Computed Tomography) examination of a patient, the method comprising:
   scanning the patient taking into account at least two different radiation spectra and reconstructing a first image on the basis of a first radiation spectrum of the at least two different radiation spectra and a second image on the basis of a second radiation spectrum of the at least two different radiation spectra;
   determining an HU (Hounsfield Unit) value diagram from the first and second image;
   determining a base gradient as a gradient of a connecting line between a first material or a first tissue type and a second material or second tissue type in the HU value diagram of the energy-specific HU values;
   selecting a first contrast agent from a number of contrast agents, each with a known enhancement gradient, with an enhancement gradient which is greater than the determined base gradient;
   selecting a second contrast agent, the enhancement gradient of which lies in a significance region of the determined base gradient; and
   generating CT images using the first and second contrast agents.

2. The method as claimed in claim 1, wherein the significance region is determined at least in respect of a subsequently performed material decomposition method, a utilized examination dose, an observed energy spectra and properties of the CT system.

3. The method as claimed in claim 2, wherein a glandular tissue is used as first tissue type.

4. The method as claimed in claim 2, wherein a liver tissue is used as first tissue type.

5. The method as claimed in claim 2, wherein a fatty tissue is used as second tissue type.

6. The method as claimed in claim 2, wherein air is used as second material.

7. The method as claimed in claim 1, wherein a glandular tissue is used as first tissue type.

8. The method as claimed in claim 1, wherein a liver tissue is used as first tissue type.

9. The method as claimed in claim 1, wherein a fatty tissue is used as second tissue type.

10. The method as claimed in claim 1, wherein air is used as second material.

11. The method as claimed in claim 1, wherein the base gradient is determined from a multiplicity of CT liver examinations with different degrees of pathological fatty metamorphosis of liver.

12. The method as claimed in claim 1, wherein an iodine-containing contrast agent is selected as first contrast agent.

13. The method as claimed in claim 12, wherein a combination of at least two lanthanides is selected in the second contrast agent.

14. The method as claimed in claim 1, wherein a contrast agent with components from the group of the lanthanides is selected as second contrast agent.

15. The method as claimed in claim 1, wherein a contrast agent which accumulates in the cardiovascular system is selected as first contrast agent.

16. The method as claimed in claim 1, wherein a contrast agent which accumulates in cells of the first tissue type is selected as second contrast agent.

17. A method for generating CT (Computed Tomography) images of a patient having two different contrast agents comprising:
   scanning the patient using a CT system, taking into account at least two different radiation spectra and reconstructing a first image on the basis of a first radiation spectrum of the at least two different radiation spectra and a second image on the basis of a second radiation spectrum of the at least two different radiation spectra;
   determining an HU (Hounsfield Unit) value diagram from the first and second image;
   wherein the second contrast of the two different contrast agents has an enhancement whose gradient in the HU value diagram corresponds to the radiation spectra of the gradient between two different materials or tissue types used in this HU value diagram,
   generating a third image solely comprising a local concentration of the first contrast agent and generating a fourth image comprising the materials or tissue types, including a local concentration of the second contrast agent, by solving linear systems of equations for each pixel or of the first and second images, which describe the relationship between absorption and components and concentration of the two tissue types and the first contrast agent; and
   output of at least one of the third and fourth image.

18. The method as claimed in claim 17, wherein the contrast agents are selected according to a method for selecting two contrast agents to be used in a dual energy CT examination of a patient comprising:
   scanning the patient taking into account at least two different radiation spectra and reconstructing the first image on the basis of a first radiation spectrum of the at least two different radiation spectra and the second image on the basis of a second radiation spectrum of the at least two different radiation spectra;

determining an HU value diagram from the first and second images;

determining a base gradient as a gradient of a connecting line between a first material or a first tissue type and a second material or second tissue type in the HU value diagram of the energy-specific HU values;

selecting a first contrast agent from a number of contrast agents, each with a known enhancement gradient, with an enhancement gradient which is greater than a determined base gradient; and selecting a second contrast agent, the enhancement gradient of which lies in a significance region of the determined base gradient.

19. The method as claimed in claim 18, wherein the following linear system of equations is solved for each pixel/voxel:

$$x_{E1}=c_{K1}*x_{K1,E1}+f*x_{G1,E1}+(1-f)*x_{G2,E1}$$

$$x_{E2}=c_{K1}*x_{K1,E2}+f*x_{G1,E2}+(1-f)*x_{G2,E2}$$

with the following variables being used:
f=proportion of the first tissue type G1,
(1−f)=proportion of the second tissue type G2,
$c_{K1}$=concentration of the first contrast agent K1,
$x_{K1,E1}$=known X-ray attenuation value of the first contrast agent K1 in respect of the first energy spectrum E1,
$x_{K1,E2}$=known X-ray attenuation value of the first contrast agent K1 in respect of the second energy spectrum E2,
$x_{G1,E1}$=known X-ray attenuation value of the first material or the first tissue type G1 in respect of the first energy spectrum E1,
$x_{G1,E2}$=known X-ray attenuation value of the first material or the first tissue type G1 in respect of the second energy spectrum E2,
$x_{G2,E1}$=known X-ray attenuation value of the second material or the second tissue type G2 in respect of the first energy spectrum E1,
$x_{G2,E2}$=known X-ray attenuation value of the second material or the second tissue type G2 in respect of the second energy spectrum E2.

20. The method as claimed in claim 17, wherein the following linear system of equations is solved for each pixel/voxel:

$$x_{E1}=c_{K1}*x_{K1,E1}+f*x_{G1,E1}+(1-f)*x_{G2,E1}$$

$$x_{E2}=c_{K1}*x_{K1,E2}+f*x_{G1,E2}+(1-f)*x_{G2,E2}$$

with the following variables being used:
f=proportion of the first tissue type G1,
(1−f)=proportion of the second tissue type G2,
$c_{K1}$=concentration of the first contrast agent K1,
$x_{K1,E1}$=known X-ray attenuation value of the first contrast agent K1 in respect of the first energy spectrum E1,
$x_{K1,E2}$=known X-ray attenuation value of the first contrast agent K1 in respect of the second energy spectrum E2,
$x_{G1,E1}$=known X-ray attenuation value of the first material or the first tissue type G1 in respect of the first energy spectrum E1,
$x_{G1,E2}$=known X-ray attenuation value of the first material or the first tissue type G1 in respect of the second energy spectrum E2,
$x_{G2,E1}$=known X-ray attenuation value of the second material or the second tissue type G2 in respect of the first energy spectrum E1,
$x_{G2,E2}$=known X-ray attenuation value of the second material or the second tissue type G2 in respect of the second energy spectrum E2.

21. The method as claimed in claim 17, wherein measurements are performed with two different energy spectra of the utilized radiation with at least one detector integrating over at least the used energy ranges in order to differentiate an absorption property of the utilized contrast agents with respect to different energy spectra.

22. The method as claimed in claim 17, wherein measurements are performed with one energy spectrum of the utilized radiation and with at least one detector selective at at least two different energy ranges in order to differentiate the absorption property of the utilized contrast agents with respect to different energy spectra.

23. A method of selecting a combination of two contrast agents, provided for application in a CT (Computed Tomography) examination of a patient comprising:

scanning the patient using a CT system, taking into account at least two different radiation spectra and discretely examine the energy spectra for assessing the proportion of a first and a second tissue type or material, with a connecting line between the first and second tissue type or material in an HU (Hounsfield Unit) value diagram of the radiation spectra;

determining a base gradient as the gradient of the connecting line;

selecting a first contrast agent having a gradient in respect of the at least two energy spectra in the HU value diagram, the gradient being greater than the base gradient;

selecting a second contrast agent having a gradient in respect of the at least two energy spectra in the HU value diagram, the gradient lying in a significance region of the base gradient; and generating CT images using the first and second contrast agents.

24. The method as claimed in claim 23, wherein at least one contrast agent comprises a single lanthanide and has the desired enhancement.

25. The method as claimed in claim 23, wherein at least one contrast agent consists of a mixture of a plurality of contrast agent components with at least differing lanthanides, wherein the individual contrast agent components have the same pharmacokinetic properties and, in total, the desired enhancement.

26. The method as claimed in claim 23, wherein at least one contrast agent comprises a molecular complex which is occupied by different contrast-providing elements with a predetermined stoichiometric ratio such that the desired enhancement is attained.

27. A method of selecting a combination of two contrast agents as claimed in claim 23 for generating CT images of a patient having two different contrast agents, wherein the second contrast of the two different contrast agents has an enhancement whose gradient in an HU value diagram corresponds to the radiation spectra of the gradient between two different materials or tissue types used in this HU value diagram, the method comprising:

scanning the patient using a CT system, taking into account at least two different radiation spectra and reconstructing a first image on the basis of a first radiation spectrum of the at least two different radiation spectra and a second image on the basis of a second radiation spectrum of the at least two different radiation spectra;

generating a third image solely comprising a local concentration of the first contrast agent and generating a fourth image comprising the materials or tissue types, including a local concentration of the second contrast agent, by solving linear systems of equations for each pixel or voxel of the first and second images, which describe the relationship between absorption and components and concentration of the two tissue types and the first contrast agent; and output of at least one of the third and fourth image.

* * * * *